United States Patent [19]

van Eekelen et al.

[11] Patent Number: 5,217,878
[45] Date of Patent: Jun. 8, 1993

[54] MOLECULAR CLONING AND EXPRESSION OF GENES ENCODING PROTEOLYTIC ENZYMES

[75] Inventors: Christiaan A. G. van Eekelen, Bergschenhoek; Johannes C. van der Laan, Amsterdam; Leo J. S. M. Mulleners, Rijen, all of Netherlands

[73] Assignee: Gist-Brocades, NV, Netherlands

[21] Appl. No.: 162,184

[22] Filed: Feb. 29, 1988

[30] Foreign Application Priority Data

Feb. 27, 1987 [EP] European Pat. Off. ........ 87200358.7

[51] Int. Cl.$^5$ ...................... C12P 24/00; C12N 15/00; B12N 15/75
[52] U.S. Cl. .............................. 435/69.1; 435/172.3; 435/221; 435/252.31; 435/320.1
[58] Field of Search .................... 435/69.1, 71.1, 71.2, 435/172.1, 172.3, 221, 252.3, 252.31, 252.33, 320, 320.1; 536/27; 935/14

[56] References Cited

U.S. PATENT DOCUMENTS 4,002,572  1/1977  te Nijenhuis ...................... 435/221

FOREIGN PATENT DOCUMENTS 0134048   3/1985  European Pat. Off. .
0283075   9/1988  European Pat. Off. .
87/04461  7/1987  World Int. Prop. O. .
88/06624  9/1988  World Int. Prop. O. ........ 435/172.3

OTHER PUBLICATIONS

Lewin; *Science* 237: 1570 (1987).
Reeck et al.; *Cell* 50: 667 (1987).
Shen et al.; *Cell* 26: 191 (1981).
Wells et al; *Nucleic Acids Res.* 11: 7911 (1983).
Stahl et al; *J. Bacteriol.* 158: 411 (1984).
Cornfield et al., "A modified protoplast-regeneration protocol facilitating the detection of cloned exoenzyme genes in *Bacillus subtilis*" *Gene* (1984) 30:17–22.
J. H. Yu et al., "Physiological properties and transformation of alkaline-tolerant bacteria" *Biological Abstracts* (1986) 82:871 Abstr. No. 86427.
Usami et al., "Plasmids in Alkalophilic Bacillus sp." *Agricultural and Biological Chemistry* (1983) 47:2101–2102.
Wong et al., "The subtilisin E gene of *Bacillus subtilis* is transcribed from a $\sigma^{37}$ promoter in vitro" *Proc. Natl. Acad. Sci. USA* (1984) 81:1184–1188.
Thomas et al., "Tailoring the pH dependence of enzyme catalysis using protein engineering" *Nature* (1985) 318:375–376.
Pak et al., "Cloning of protease gene produced by heat-resistant alkalinic Bacillus in *Escherichia coli*" *Biological Abstracts/RRM*, Ref No. 34060253 title only.
Horikoshi et al., "Genetic Applications of Alkalophilic Microorganisms" *Spec. Publ. Soc. Gen. Microbiol.* (1986) 17:297–315.
Vasantha et al., "Cloning of a Serine Protease Gene from *Bacillus amyloliquefaciens* and Its Expression in *Bacillus subtilis*" *Genetics and Biotechnology of Bacilli* (Proc. Int. Conf. 2nd International Conf. (Jul. 1983) pp. 163–172.
Hofemeister et al., "Integration of plasmid pE194 at multiple sites on the *Bacillus subtilis* chromosomes" *Chemical Abstracts* (1983) 98:88.
Prozorov et al., "Insertion of eukaryotic DNA into the *Bacillus subtilis* genome by means of a temperature-sensitive plasmid vector" *Gene* (1985) 34:39–46.

*Primary Examiner*—James Martinell
*Attorney, Agent, or Firm*—Barbara Rae-Venter; Bertram I. Rowland

[57] ABSTRACT

Novel methods and novel industrial Bacillus strains are provided for enhanced production of serine protease. Plasmid constructs comprising the serine protease gene are introduced into a compatible host, generally a Bacillus already overproducing serine protease. Preferred host cells are those from Bacillus novo sp. PB92 and the preferred serine protease gene also originates from Bacillus PB92. Integration and maintenance of the plasmid in the host cell chromosome can be achieved by including a temperature sensitive origin of replication in the plasmid construct and growing under selective conditions.

18 Claims, 6 Drawing Sheets

```
                                                        P1
         20                        40                        60
GATTCTGTTAACTTAACGTTAATATTTGTTTCCCAATAGGCAAATCTTTCTAACTTTGAT
                                        ―――――――

P2                                RBS              Pre
         80                        100                    ┌─120
ACGGTTTAAACTACCAGCTTGGACAAGTTGGGATAAAAATGAGGAGGGAACCGAATGAAG
―――――――                             ―――――――――                  MetLys
      1.
         140                        160                    180
                ――――――――――
AAACCGTTGGGGAAAATTGTCGCAAGCACCGCACTACTCATTTCTGTTGCTTTTAGTTCA

LysProLeuGlyLysIleValAlaSerThrAlaLeuLeuIleSerValAlaPheSerSer

Pro                                 2.
                ┌─200─           220                       240
                                                   ――――――――――
TCGATCGCATCGGCTGCTGAAGAAGCAAAAGAAAAATATTTAATTGGCTTTAATGAGCAG

SerIleAlaSerAlaAlaGluGluAlaLysGluLysTyrLeuIleGlyPheAsnGluGln 260                        280                    300
――
GAAGCTGTCAGTGAGTTTGTAGAACAAGTAGAGGCAAATGACGAGGTCGCCATTCTCTCT

GluAlaValSerGluPheValGluGlnValGluAlaAsnAspGluValAlaIleLeuSer 3.
         320                        340                    360
                                    ――――――――――――――
GAGGAAGAGGAAGTCGAAATTGAATTGCTTCATGAATTTGAAACGATTCCTGTTTTATCC

GluGluGluGluValGluIleGluLeuLeuHisGluPheGluThrIleProValLeuSer 380                        400                    420
GTTGAGTTAAGCCCAGAAGATGTGGACGCGCTTGAACTCGATCCAGCGATTTCTTATATT

ValGluLeuSerProGluAspValAspAlaLeuGluLeuAspProAlaIleSerTyrIle mat      4.
         440                ┌──────460                     480
                            │    ―――――――――――
GAAGAGGATGCAGAAGTAACGACAATGGCGCAATCAGTGCCATGGGGAATTAGCCGTGTG GluGluAspAlaGluValThrThrMetAlaGlnSerValProTrpGlyIleSerArgVal
```

FIG. 3a

```
                     500            520            540
CAAGCCCCAGCTGCCCATAACCGTGGATTGACAGGTTCTGGTGTAAAAGTTGCTGTCCTC
GlnAlaProAlaAlaHisAsnArgGlyLeuThrGlySerGlyValLysValAlaValLeu
                      5.
                     560            580            600
GATACAGGTATTTCCACTCATCCAGACTTAAATATTCGTGGTGGCGCTAGCTTTGTACCA
AspThrGlyIleSerThrHisProAspLeuAsnIleArgGlyGlyAlaSerPheValPro 620            640            660
GGGGAACCATCCACTCAAGATGGGAATGGGCATGGCACGCATGTGGCTGGGACGATTGCT
GlyGluProSerThrGlnAspGlyAsnGlyHisGlyThrHisValAlaGlyThrIleAla
         6.
                     680            700            720
GCTTTAAACAATTCGATTGGCGTTCTTGGCGTAGCACCGAACGCGGAACTATACGCTGTT
AlaLeuAsnAsnSerIleGlyValLeuGlyValAlaProAsnAlaGluLeuTyrAlaVal 740            760            780
AAAGTATTAGGGGCGAGCGGTTCAGGTTCGGTCAGCTCGATTGCCCAAGGATTGGAATGG
LysValLeuGlyAlaSerGlySerGlySerValSerSerIleAlaGlnGlyLeuGluTrp
              7.
                     800            820            840
GCAGGGAACAATGGCATGCACGTTGCTAATTTGAGTTTAGGAAGCCCTTCGCCAAGTGCC
AlaGlyAsnAsnGlyMetHisValAlaAsnLeuSerLeuGlySerProSerProSerAla 860            880            900
ACACTTGAGCAAGCTGTTAATAGCGCGACTTCTAGAGGCGTTCTTGTTGTAGCGGCATCT
ThrLeuGluGlnAlaValAsnSerAlaThrSerArgGlyValLeuValValAlaAlaSer
                       8.
                     920            940            960
GGGAATTCAGGTGCAGGCTCAATCAGCTATCCGGCCCGTTATGCGAACGCAATGGCAGTC
GlyAsnSerGlyAlaGlySerIleSerTyrProAlaArgTyrAlaAsnAlaMetAlaVal
```

FIG. 3b

```
                    980                   1000                  1020
GGAGCTACTGACCAAAACAACAACCGCGCCAGCTTTTCACAGTATGGCGCAGGGCTTGAC
GlyAlaThrAspGlnAsnAsnAsnArgAlaSerPheSerGlnTyrGlyAlaGlyLeuAsp
          9.
                   1040                  1060                  1080
ATTGTCGCACCAGGTGTAAACGTGCAGAGCACATACCCAGGTTCAACGTATGCCAGCTTA
IleValAlaProGlyValAsnValGlnSerThrTyrProGlySerThrTyrAlaSerLeu
                                                          10.
                   1100                  1120                  1140
AACGGTACATCGATGGCTACTCCTCATGTTGCAGGTGCAGCAGCCCTTGTTAAACAAAAG
AsnGlyThrSerMetAlaThrProHisValAlaGlyAlaAlaAlaLeuValLysGlnLys 1160                  1180                  1200
AACCCATCTTGGTCCAATGTACAAATCCGCAATCATCTAAAGAATACGGCAACGAGCTTG
AsnProSerTrpSerAsnValGlnIleArgAsnHisLeuLysAsnThrAlaThrSerLeu 1220                  1240                  1260
GGAAGCACGAACTTGTATGGAAGCGGACTTGTCAATGCAGAAGCGGCAACACGCTAATCA
GlySerThrAsnLeuTyrGlySerGlyLeuValAsnAlaGluAlaAlaThrArg 1280                  1300                  1320
ATAAAAACGCTGTGCTTAAAGGGCACAGCGTTTTTTTGTGTATGAATCGAAAAAGAGAAC
             terminator
```

FIG. 3c

MOLECULAR CLONING AND EXPRESSION OF GENES ENCODING PROTEOLYTIC ENZYMES

INTRODUCTION

1. Technical Field

The field of this invention relates to enhanced production of serine protease in Bacillus strains employing recombinant techniques.

2. Background

Bacilli have been used widely for the production of industrially important enzymes such as α-amylase, neutral protease and alkaline or serine proteases. In general, bacterial serine proteases can be obtained from many prokaryotic organisms including gram negative organisms such as Serratia or Pseudomonas species and gram positive bacteria such as Micrococcus and Bacillus species. A group of industrially important serine proteases of particular interest are those which have high activity in alkaline media. While industrial serine proteases are produced by various Bacillus species, including *B. subtilis*, *B. licheniformis*, *B. amyloliquefaciens*, *B. alcalophilus* and other Bacillus species, the high alkaline proteases are generally produced by Bacillus strains which are capable of growing at alkaline pH. An example of such a bacillus is Bacillus novo species PB92.

There is a substantial interest in developing strains of bacilli capable of producing proteolytic enzymes in high yield, particularly high alkaline proteases.

RELEVANT LITERATURE

Several genes for extracellular enzymes of bacilli have been successfully cloned, such as the α-amylase genes of *B. amyloliquefaciens* (Palva et al., *Gene* (1981) 15:43-51), *B. licheniformis* (Ortlepp, *Gene* (1983) 23:267), *B. stearothermophilus* (Mielenz et al., *Proc. Natl. Acad. Sci. USA* (1983) 80:5975-5979: EPA-0057976) and *B. subtilis* (Yang et al., *Nucleic Acids Res.* (1983) 11:237): the levansucrase gene of *B. subtilis* (Gay et al., *J. Bacteriol.* (1983) 153:1424): the neutral protease encoding genes of *B. stearothermophilus* (Fuji et al., *J. Bacteriol.* (1983) 156:831), *B. amyloliquefaciens* (Honjo et al., *J. Biotech.* (1984) 1:165) and of *B. subtilis* (Yang et al., *J. Bacteriol.* (1984) 160:115: the serine or alkaline protease encoding genes of *B. subtilis* (Wong et al., *Proc. Natl. Acad. Sci. USA* (1984) 81:1184), *B. licheniformis* (Jacobs et al., *Nucleic Acids Res.* (1985) 13:8913) and *B. amyloliquefaciens* (Wells et al., *Nucleic Acids Res.* (1983) 11:7.911).

Production of industrial serine proteases in various Bacillus species is described in, for example, U.S. Pat. Nos. 3,674,643; 3,723,250: and 4,480,043. Production of high alkaline proteolytic enzyme by Bacillus strains capable of growing at alkaline pH is described in, for example, U.S. Pat. Nos. 3,723,250: Re. 30,602 and 4,480,037. For a review article of the use of bacilli for production of industrially important enzymes see, for example, Debabov, "The Industrial Use of Bacilli" in: The Molecular Biology of Bacilli, [Academic Press, New York, 1982].

A protocol for protoplast transformation of *B. subtilis* is described by Chang and Cohen, *Mol. Gen. Genet.* (1979) 168:111-115. Similar protocols have been described for the successful transformation of *B. megaterium* protoplasts (Vorobjeva et al., *FEMS Microbiol. Letters* (1980) 7:261-263), *B. amyloliquefaciens* protoplasts (Smith et al., *Appl. and Env. Microbiol.* (1986) 51:634), *B. thuringiensis* (Fisher et al., *Arch. Microbiol.* (1981) 139:213-217), *B. sphaericus* protoplasts (McDonald, *J. Gen. Microbiol.* (1984) 130:203) and *B. larvae* protoplasts (Bakhiet et al., *Appl. and Env. Microbiol.* (1985) 49:577). However, Bakhiet et al. (supra.) reported unsuccessful results with *B. popillae*. Mann et al., *Current Microbiol.* (1986) 13:131-135 reported successful transformation with *B. polymixa*, *B. licheniformis*, *B. macerans* and *B. laterosporus*. However, the protocol was not successful with *B. coagulans*, *B. cereus* and *B. pumilus* even though good protoplast formation was observed. Other methods for introducing DNA into protoplasts include fusion with DNA containing liposomes. Holubova, *Folia Microbiol.* (1985) 30:97.

SUMMARY OF THE INVENTION

Novel alkalophilic Bacillus strains, methods and compositions for transforming such strains, are provided. A novel DNA sequence is also provided, said DNA sequence comprising a gene encoding a high alkaline proteolytic enzyme derived from an alkalophilic Bacillus strain. A host cell, preferably having a positive background, is transformed using a plasmid construct comprising a gene encoding said high alkaline proteolytic enzyme. Protoplast transformation with the plasmid construct in the presence of polyethylene glycol at alkaline pH may be employed. The DNA sequence may be maintained extrachromosomally, or integrated into the host cell genome.

DESCRIPTION OF THE DRAWINGS

BRIEF

Figure 1:
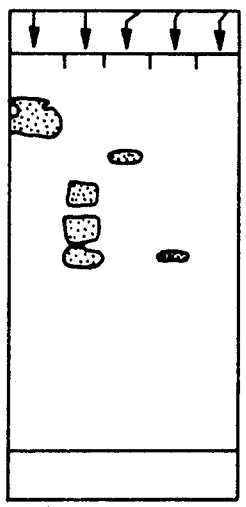

FIG. 1 shows the results of histidine/MOPS gel electrophoresis performed on supernatants from cultures of *B. subtilis* DB104 containing pUB110 and pM58, respectively, compared with several subtilisins.

lane 1: Carlsberg subtilisin
lane 2: Bacillus PB92 protease
lane 3 *Bacillus subtilis* subtilisin
lane 4: *Bacillus subtilis* DB104 (pM58)
lane 5: *Bacillus subtilis* DB104 (pUB110)

Figure 2A:
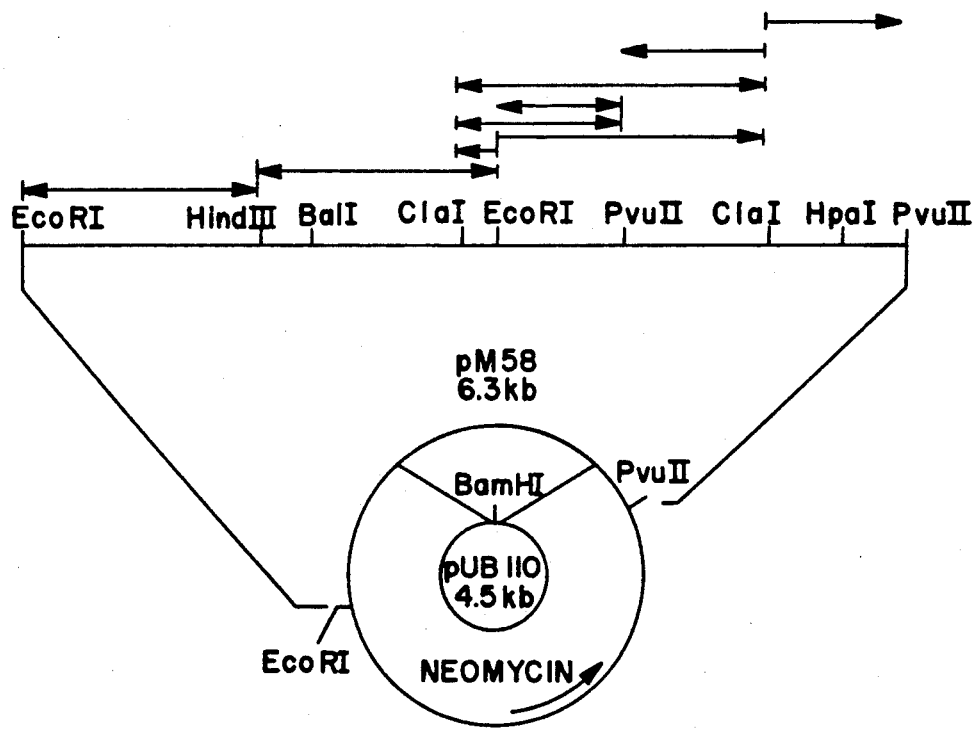
Figure 2B:
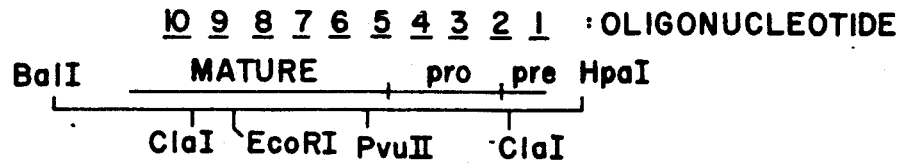

FIG. 2 shows the restriction map of plasmid pM58. Furthermore, the sequencing strategy is shown in FIG. 2a. The arrowed solid lines represent the fragments cloned in the phage M13 vectors mp10, mp11 and mp18. The lower part of the FIG. 2b shows the sequencing strategy using 10 oligonucleotides located at regular distances on the protease gene.

FIG. 3(a, b and c) shows the nucleotide sequence of the coding strand correlated with the amino acid sequence of the Bacillus PB92 serine protease. Promoters ($P_1$, $P_2$), ribosome binding site (rbs) and termination regions (term) of the DNA sequence are also shown. The numbered solid lines represent the location of the ten oligonucleotides used for sequencing.

Figure 4A:
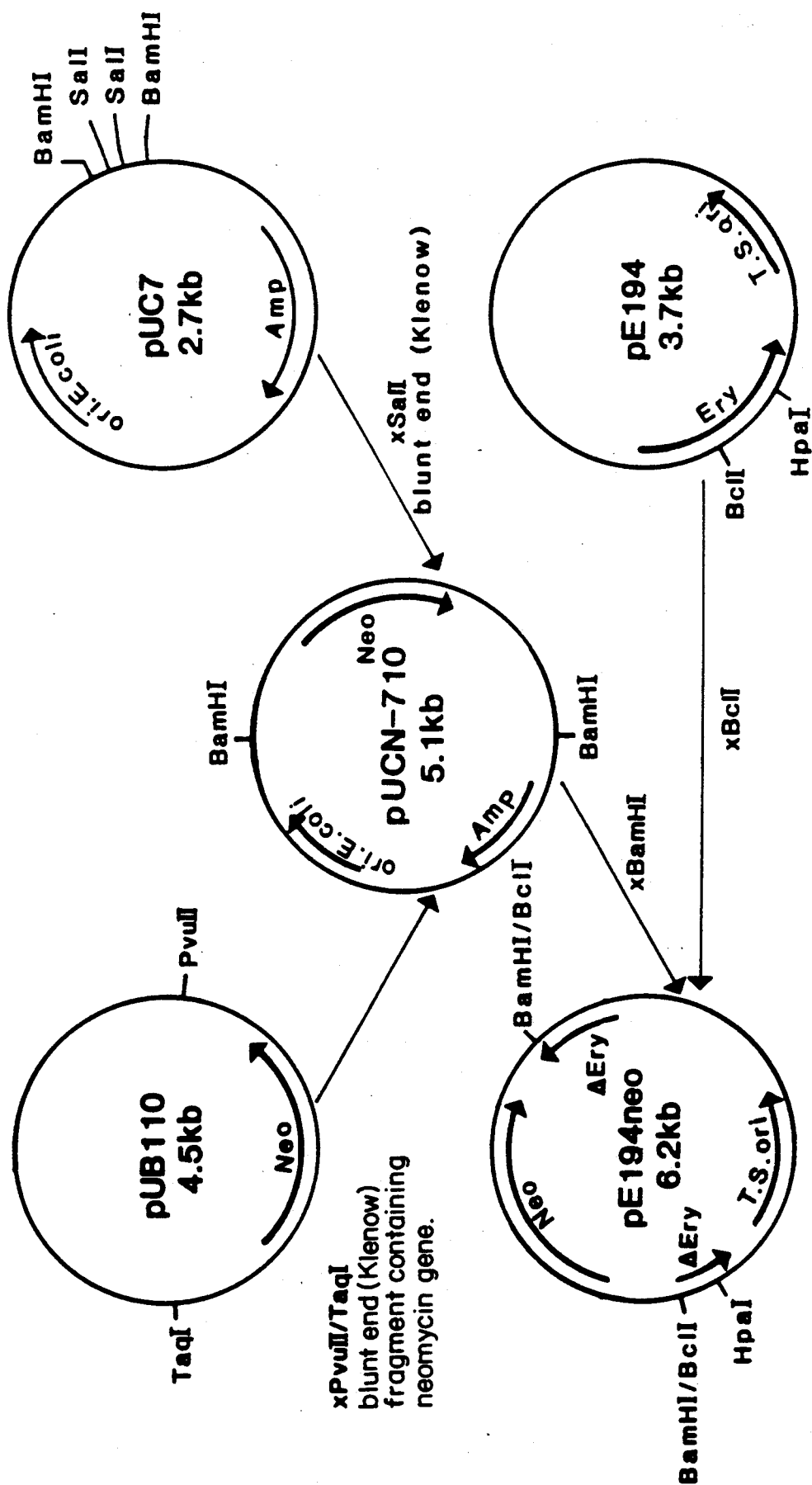

FIG. 4a shows the construction of plasmid pE194-neo.

Figure 4B:
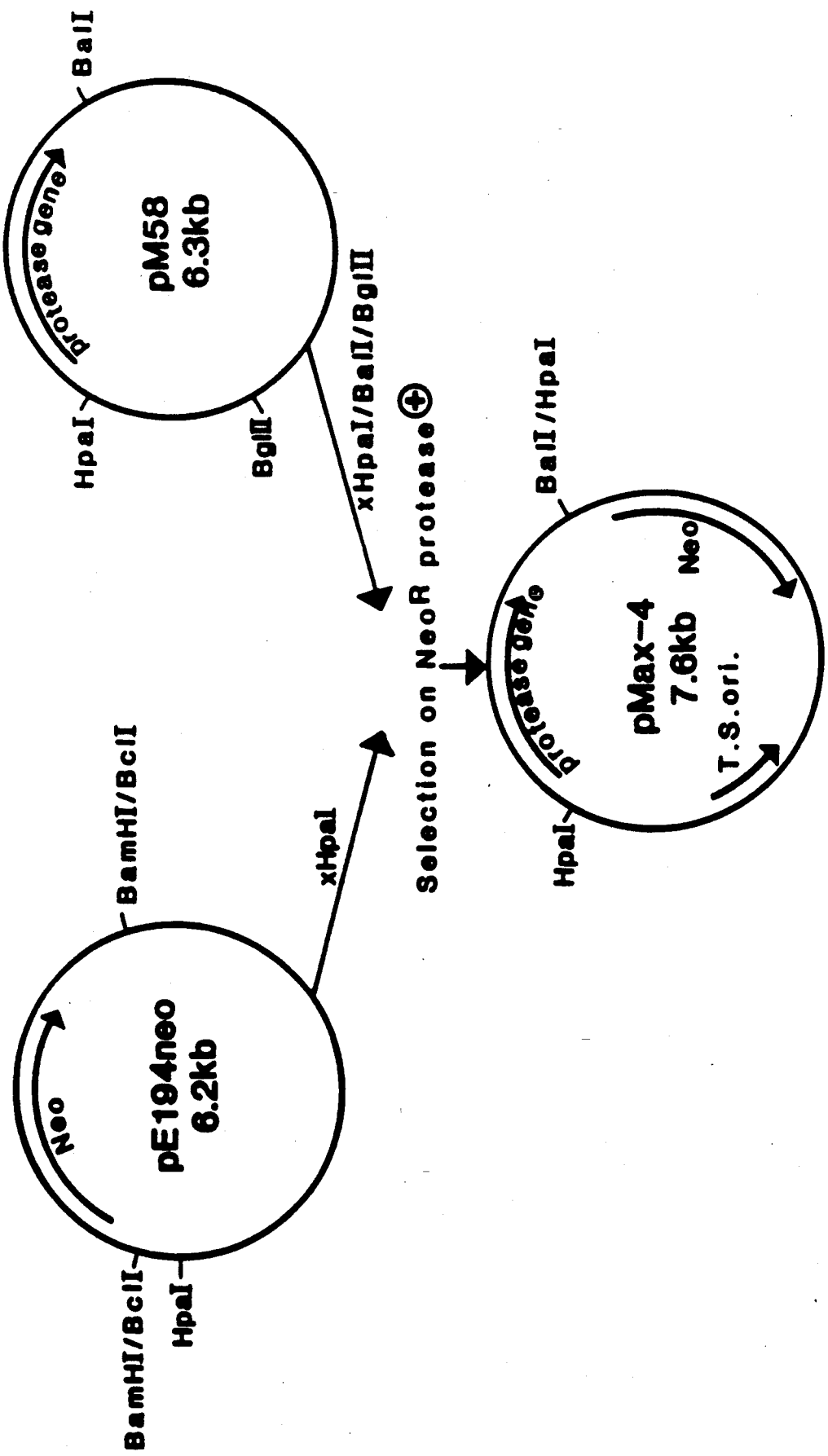

FIG. 4b shows the construction of plasmid pMAX-4.

DESCRIPTION OF THE SPECIFIC EMBODIMENTS

In accordance with the subject invention, novel DNA constructs and Bacillus strains, for producing proteolytic enzymes in high yield, as well as methods for their preparation are provided. Host cells are transformed by combining protoplasts prepared from the host Bacillus strain under fusing conditions with a plasmid construct comprising a DNA sequence encoding a proteolytic enzyme.

High alkaline proteases are serine proteases or subtilisins with high activity in alkaline media. More specifically, high alkaline proteases have an optimal activity at pH values higher than about 9 and retain at least 80% of this optimal activity at a pH of about 11 or even higher. High alkaline proteases are generally produced by Bacillus strains which are capable of growing at alkaline pH.

The techniques used in isolating the protease gene are known in the art, including synthesis, isolation from genomic DNA, preparation from cDNA, or combinations thereof. Isolation and expression of high alkaline protease genes are disclosed in the priority document upon which this application is based, European Application No. EP-A-87200358.7, which disclosure is incorporated herein by reference. The various techniques for manipulation of the genes are well known, and include restriction, digestion, resection, ligation, in vitro mutagenesis, primer repair, employing linkers and adapters, and the like. See Maniatis et al., Molecular Cloning, Cold Spring Harbor Laboratory, Cold Spring Harbor, N.Y., 1982.

Generally, the method comprises preparing a genomic library from an organism expressing a high alkaline protease. The genome of the donor microorganism is isolated and cleaved by an appropriate restriction enzyme. The resulting DNA fragments of the donor strain are then ligated into a cloning vector which has been cleaved with a compatible restriction endonuclease.

Clones containing the inserted DNA fragment may be identified by means of a resistance marker or by using a direct or positive selection procedure such as that developed for B. subtilis (Gryczan and Dubnow, Gene (1982) 20:459-469). In addition, clones expressing a high alkaline protease may be identified by the use of antibodies directed to the expression product, or detection of loss of substrate or formation of product of the proteolytic enzyme. For example, colonies expressing a marker gene such as antibiotic resistance may be screened for protease production as determined by increased precipitation of a halo of casein around colonies plated on agar plates containing casein.

Once a complete gene has been identified, either as cDNA or chromosomal DNA, it may then be manipulated in a variety of ways to provide for expression. Bacillus hosts may be employed which include, for example, alkalophilic bacteria, including those alkalophilic bacilli which are already high alkaline protease producers. A preferred host organism is Bacillus novo sp. PB92. It is therefore convenient to maintain the wild-type sequence with regulatory signals and secretory leader sequence, etc., although control regions derived from other bacilli which are functional in the Bacillus host strain can also be used. A suitable vector for transforming a Bacillus cell thus includes a structural gene encoding a high alkaline protease obtainable from an alkalophilic Bacillus including control regions such as a promoter sequence, a sequence forming the ribosomal binding site and sequences controlling termination of transcription and translation of the alkaline protease gene, said control regions being functional in an alkalophilic Bacillus host cell.

The vector additionally may include a marker gene, for example for conferring resistance to an antibiotic to which the host strain is sensitive, and an origin of replication that is capable of replicating autonomously in the host cell. The origin of replication may be one having a mutation which makes its functioning temperature-sensitive in the host cell, thus enabling selection for chromosomal integration as described by Ehrlich, Proc. Natl. Acad. Sci. USA (1978) 75:1433.

The amino acid sequence can be used to design a probe to screen a cDNA or a genomic library prepared from mRNA or DNA from cells of interest as donor cells for a high alkaline protease gene. By using the high alkaline protease cDNA or a fragment thereof as a hybridization probe, structurally related genes found in other organisms can easily be cloned. Of particular interest is the isolation of genes from organisms that express high alkaline serine proteases by using oligonucleotide probes based on the nucleotide sequences of high alkaline serine protease genes obtainable from alkalophilic Bacillus strains, including Bacillus novo species PB92. Such probes can be considerably shorter than the entire sequence but should be at least 10, preferably at least 15, more preferably 20 nucleotides in length. Longer oligonucleotides are also useful, up to the full length of the gene, preferably no more than 1200 nucleotides in length. Both RNA and DNA probes can be used.

In use, the probes are typically labeled in a detectable manner (e.g., with $^{32}P$, $^3H$, biotin, or avidin) and are incubated with single-stranded DNA or RNA from the organism in which a gene is sought. Hybridization is detected by means of the label after single-stranded and double-stranded (hybridized) DNA (or DNA/RNA) have been separated (typically using nitrocellulose paper). Hybridization techniques suitable for use with oligonucleotides are well known to those skilled in the art.

Although probes are normally used with a detectable label which permits easy identification, unlabeled oligonucleotides are also useful, both as precursors of labeled probes and for use in methods that provide for direct detection of double-stranded DNA (or DNA/RNA). Accordingly, the term oligonucleotide probe refers to both labeled and unlabeled forms. The ligation mixture is then used to transform competent B. subtilis cells. Using the marker gene as a means of selection, recombinant plasmids can then be isolated and characterized by restriction analysis and sequencing.

For high alkaline protease production, a preferred DNA sequence for use in transforming Bacillus strains which already produce serine protease is a sequence originating from Bacillus novo species PB92. The amino acid sequence of the serine protease encoded by the DNA sequence is as follows:

H₂N-A-Q-S-V-P-W-G-I-S-R-V-Q-A-P-A-A-H-N-R-G-L-T-G-S-G-
V-K-V-A-V-L-D-T-G-I-S-T-H-P-D-L-N-I-R-G-G-A-S-F-V-P-G-
E-P-S-T-Q-D-G-N-G-H-G-T-H-V-A-G-T-I-A-A-L-N-N-S-I-G-V-
L-G-V-A-P-N-A-E-L-Y-A-V-K-V-L-G-A-S-G-S-G-S-V-S-S-I-A-
Q-G-L-E-W-A-G-N-N-G-M-H-V-A-N-L-S-L-G-S-P-S-P-S-A-T-L-
E-Q-A-V-N-S-A-T-S-R-G-V-L-V-V-A-A-S-G-N-S-G-A-G-S-I-S-
Y-P-A-R-Y-A-N-A-M-A-V-G-A-T-D-Q-N-N-N-R-A-S-F-S-Q-Y-G-
A-G-L-D-I-V-A-P-G-V-N-V-Q-S-T-Y-P-G-S-T-Y-A-S-L-N-G-T-
S-M-A-T-P-H-V-A-G-A-A-A-L-V-K-Q-K-N-P-S-W-S-N-V-Q-I-R-
N-H-L-K-N-T-A-T-S-L-G-S-T-N-L-Y-G-S-G-L-V-N-A-E-A-A-T-
R-COOH.

While the preferred strain for providing the protease gene is Bacillus novo species PB92, essentially the same serine protease may be obtained from other alkalophilic bacilli. Such protease genes, having at least about 70% and preferably from about 80% homology with the amino acid sequence of Bacillus PB92, are to be understood as within the scope of the present invention.

It is desirable that the expression product be secreted. Since the alkaline protease is secreted, the wild-type secretory leader signals and processing signals can be used. In addition, a fused gene may be prepared by providing a 5' sequence to the structural gene which encodes a secretory leader and a processing signal. Illustrative heterologous secretory leaders include the secretory leaders of Bacillus amylase and protease genes. By fusion in proper reading frame of the secretory leader with the structural gene of interest, the mature alkalophilic protease may be secreted into the culture medium.

The expression cassette may be wholly or partially derived from natural sources, and either wholly or partially derived from sources homologous to the host cell, or heterologous to the host cell. The various DNA constructs (DNA sequences, vectors, plasmids, expression cassettes) of the invention are isolated and/or purified, or synthesized and thus are not "naturally-occurring".

Depending upon whether integration of the structural gene into the chromosome of the host strain or maintenance on an extrachromosomal element is desired, a replication system for Bacillus may or may not be included. For integration, stretches of homology in the plasmid construct with the Bacillus genome may be used to enhance the probability of recombination. Furthermore, inclusion of a temperature-sensitive origin of replication in the plasmid constructor permits selection for chromosomal integration. See for example, Erlich, *Proc. Natl. Acad. Sci. USA* (1978) 75:1433.

More than one copy of the structural gene can be inserted into the host cell to amplify expression of the structural gene. Stable amplification of the structural gene can be obtained by integrating at least one additional copy of the structural gene into the host cell genome and selecting for tranformants in which copies of the structural gene are separated by endogenous chromosomal sequences. DNA constructs and methods for prokaryotic systems are described in European Application No. EP-A-87200356.1, which disclosure is incorporated herein by reference.

In addition to the replication system, there will usually be at least one marker gene included in the plasmid construct. By marker gene is intended a structural gene capable of expression in a host which provides for biocide or viral resistance, resistance to heavy metals, immunity, and the like. For biocide resistance, this may include resistance to antibiotics, for example, neomycin, kanamycin, tetracycline, etc. The marker gene will be selected to provide selection at low copy number at an antibiotic concentration which does not seriously impede growth of recombinant cells. Of particular interest is resistance to neomycin.

The various DNA sequences may be derived from diverse sources and joined together to provide for a vector which includes one or more convenient, preferably unique, restriction sites to allow for insertion or substitution of the structural genes at such sites to provide the plasmid construct.

Once the plasmid construct has been prepared, it can be used for transforming an appropriate host cell. The host Bacillus may be any Bacillus strain, however choice of an appropriate strain takes into account factors which can improve production of high alkaline proteases. Production can be improved in a variety of ways, including using a host in which there is reduced degradation of the desired product, recognition of regulatory signals, ease of secretion, etc. Thus, while a preferred host Bacillus is a high alkaline protease producer, either a wild-type Bacillus or a mutant Bacillus, the host Bacillus can also be a high alkaline protease producer mutant which does not produce high alkaline protease. The host Bacillus strain may include a wild-type strain, which prior to transformation, produces a serine protease. Also included are mutant Bacillus strains of a wild-type strain which produces serine protease; untransformed cells of the mutant strain may be either producers or non-producers of serine protease.

High alkaline protease producing bacilli are taxonomically not well classified and are generally referred to as alkalophilic Bacillus strains. Examples of Bacillus strains capable of growing at alkaline pH are described in, for example, U.S. Pat. Nos. 3,723,250; Re. 30,602 and 4,480,037. An example of a preferred alkalophilic Bacillus host strain is strain Bacillus novo species PB92 disclosed inter alia in U.S. Pat. No. Re. 30,602.

Industrial alkalophilic Bacillus strains can also be used as host cells. Industrial Bacillus strains originate from organisms which may be isolated in the soil or are available from depositories or other sources and are obtained by genetic modification of such Bacillus strains. The industrial Bacillus strains are characterized by being resistant to genetic exchange, such as phage infection or transformation. The strains are stable and may or may not be capable of spore formation. They are usually prototrophic and modified to provide for high yields of endogenous protein products, such as the enzymes α-amylase and various proteases. The yield of an endogenous protein product obtained in an industrial production process can amount to at least 5 g/l (0.5% w/v). Industrial strains also secrete DNases, which result in the degradation of DNA in the medium, providing for protection against genetic exchange.

Transformation of alkalophilic Bacillus strains will preferably involve the use of protoplasts from said strains. However, the conventional protoplast transformation protocol as described by Cohen et al., supra., does not work for alkalophilic Bacillus strains. Therefore additional protocols had to be developed.

For alkalophilic bacilli, formation and regeneration of protoplasts can occur at high pH, preferably at about pH 8. Protoplasts can be prepared by resuspending the cells in an alkaline holding medium (AHM), pH 7.8 to 8.5, then incubating the cells for 30-80 mins at 37° C. For an example of an AHM, see Example 5. The resulting protoplasts are then washed to remove lysozyme, then resuspended in AHM. The plasmid construct and the alkalophilic Bacillus host protoplast are then combined in the presence of an appropriate fusogen. While any fusogen may be employed which provides the desired efficiency, for the most part polyethylene glycol (mw 1000-8000) is found to provide high efficiency fusion with great convenience. Protoplasts prepared from the Bacillus acceptor strain are mixed with the plasmid construct for not more than 5 minutes, preferably no longer than 2 minutes in the presence of polyethylene glycol. The fusogen mixture is then replaced with a conventional nutrient medium in which the cells are incubated for up to 5 hours, preferably 2-3 hours, before transfer to regeneration plates. The regeneration plates contain an antibiotic such as neomycin for selection of transformants.

Clones with episomal maintenance of the DNA construct may be identified by detection of expression of the high alkaline serine protease. To identify those clones which contain the expression construct as an integral part of their chromosomes, clones which develop are screened by isolation of total cellular DNA and selection for those clones in which no free plasmid DNA can be detected, but the marker gene of the plasmid is expressed. The clones may then be screened in appropriate ways for detection of the expression of the high alkaline serine protease.

Various detection techniques which may be used include use of specific antibodies, DNA or RNA hybridization, formation of enzyme product or disappearance of enzyme substrate. These techniques may be employed for screening the clones to determine the presence of the expression construct and expression of the structural gene of interest, namely protease production. The protease produced can be characterized biochemically by, for example, determination of molecular weight of the protease on SDS-polyacrylamide gel electrophoresis, histidine-MOPS gel electrophoresis and determination of the kinetic parameters $K_m$ and $V_{max}$, assayed on the synthetic substrate succinyl-L-alanyl-L-alanyl-L-prolyl-L-phenylalanyl-p-nitro-anilide.

The Bacillus host containing the expression construct episomally or chromosomally integrated is then grown in a nutrient medium under conditions which favor enzyme synthesis. The nutrient medium usually will include a means of maintaining the plasmid, such as the presence of an antibiotic to which the untransformed host is sensitive. The fermenting may be continued until the broth is exhausted. Where the product has been secreted, the product may be isolated from the broth by conventional techniques, for example by extraction, chromatography, electrophoresis, or the like. Where the product is retained in the cytoplasm, the may be harvested by centrifugation, filtration, etc., lysed by mechanical shearing, detergent, lysozyme, or other techniques and the product isolated as described previously. When the untransformed host cell is a high alkaline protease producer, by employing the subject method greatly enhanced yields of high alkaline serine protease can be achieved, usually at least about 120% as compared to the yield of the untransformed host cell, with a single extrachromosomal gene copy.

The following examples are offered by way of illustration and not by way of limitation.

EXPERIMENTAL

Example 1

Preparation of a Genomic DNA Library from Alkalophilic Bacillus novo sp. PB92 and Isolation of the Serine Protease Gene Chromosomal DNA was isolated from Bacillus novo sp. PB92 (deposited under No. OR-60 with Laboratorium voor Microbiologie, Technical University of Delft, the Netherlands, see U.S. Pat. No. Re. 30,602) according to the procedure described by Saito-Miuva, *Biochim. Biophys. Acta* (1963) 72:619–632. The DNA was partially digested with the restriction enzyme Sau3A and ligated into the BamHI site of plasmid pUB110 (Gryczan et al., *J. Bacteriol.* (1978) 124:318–329). pUB110 plasmid DNA was prepared as described by Birnboim and Doly (*Nucleic Acids Res.* (1979) 7:1513–1523).

The ligation mixture was transformed into *B. subtilis* 1A40 (Bacillus Genetic Stock Center) according to the method of Spizizen et al., *J. Bacteriol.* (1961) 81:741–746, using 0.6–1 µg DNA per ml of competent cells. Cells from the transformation mixture were plated on minimal plates containing: 2.8% $K_2HPO_4$, 1.2% $KH_2PO_4$, 0.4% $(NH_4)_2SO_4$, 0.2% tri-Na-citrate.2$H_2O$, 0.04% $MgSO_4.7H_2O$, 0.00005% $MnSO_4.4H_2O$, 0.4% L-glutamic acid, 0.5% glucose, 0.02% casamino acids, 50 pg/ml tryptophan, 20 µg/ml methionine, 20 µg/ml lysine, 20 µg/ml neomycin, 0.4% casein and 1.5% agar. After overnight incubation of the plates at 37° C., one out of 50,000 neomycin resistant colonies showed increased protease production, as determined by increased precipitation of a halo of casein cleavage products around the colony in the agar plate. Plasmid DNA was isolated from this colony according to the method described by Birnboim and Doly, *Nucleic Acids Res.* (1979) 7:1513–1523, and named pM58.

Example 2

Expression of the PB92 Serine Protease Gene

*Bacillus subtilis* 1A40 containing pM58 was grown in minimal medium (Spizizen et al., *Proc. Natl. Acad. Sci. USA* (1958) 44:1072–1078) to which had been added 0.02% casamino acids, 50 µg/ml tryptophan, 20 µg/ml methionine, 20 µg/ml lysine and 20 µg/ml neomycin. After 24 hours, the culture was centrifuged and the supernatant assayed for protease activity using dimethyl casein as substrate (Lin et al., *J. Biol. Chem.* (1969) 244:789–793. A control culture of *B. subtilis* 1A40 containing the plasmid pUB110 showed less than 1/60 of the protease activity shown by the pM58 transformed culture. Protease activity was completely inhibited by treatment with 1 mM phenylsulfonyl fluoride (PMSF), but not by treatment with 20 mM EDTA.

Aliquots of the above described supernatants were analyzed on protein gels according to the method of Laemmli, *Nature* (1970) 227:680. Samples for analysis on these gels were prepared by treatment of the supernatants with 5% trichloroacetic acid (TCA). Following centrifugation of the sample, the pellet of precipitated protein was washed twice with acetone then dissolved in 40 µl sample buffer (0.5M Tris/HCl, pH 7.5, 10% v/v 2-mercaptoethanol, 50% v/v glycerol and 0.05% Bromophenol Blue) by boiling for 10 minutes. Culture supernatant samples were then analyzed by electrophoresis. Three different *B. subtilis* 1A40 strains were used: a strain containing pUB110: or pM58: or no plasmid: and Bacillus PB92 protease as a control. After electrophoresis, the gels were stained using Commassie Brilliant Blue and destained. The sample from *B. subtilis* strain 1A40 containing pM58 contained a 31 kD protein, which comigrates with Bacillus PB92 protease. This protein was not detected on the control lane of strain *B. subtilis* 1A40 containing pUB110.

All serine proteases have similar molecular weights. The cloned serine protease of Bacillus PB92 therefore was differentiated from known serine proteases (*B. subtilis* subtilisin, Carlsberg subtilisin), by transformation of pM58 and pUB110 to the protease negative *B. subtilis* strain DB104 (Doi, *J. Bacteriol.* (1984) 60:442–444) and analysis of the extracellular proteases produced. The obtained transformants were grown in minimal medium (Spizizen et al., *Proc. Natl. Acad. Sci. USA* (1958) 44:1072–1078) containing 0.02% casamino acids, 50 µg/ml histidine and 20 µg/ml neomycin. After 24 hours, samples were taken, centrifuged and without pretreatment analyzed on histidine/MOPS gels containing 75 mM KOH, 40 mM histidine, 100 mM MOPS (3-(N-morpholino)-propanesulfonic acid), pH 7.5 and 5% polyacrylamide. Electrophoresis buffer contained 40 mM histidine, 100 mM MOPS, pH 6.6. Samples were run in the direction of the cathode. Protease bands were detected with Agfa Pan 100 Professional films (Zuidweg et al., *Biotechnol. and Bioengin.* (1972) 14:685–714). These results are shown in FIG. 1. As shown, pM58 harbors the gene encoding Bacillus PB92 protease.

Example 3

Sequencing of the Bacillus PB92 Serine Protease Gene

The entire sequence of a BalI-HpaI fragment of pM58 was determined by the method of F. Sanger, *Proc. Natl. Acad. Sci. USA* (1977) 74:6463. Restriction fragments of pM58 (see FIG. 2) were cloned in phage M13 vectors mp10, mp11 and mp18 (Messing et al., *Nucleic Acids Res.* (1981) 9:309–321. Insertions of pM58 fragments were screened by plaque hybridization. After sequencing, ten oligonucleotides located at regular distances on the gene were made and sequencing was repeated, confirming the sequence shown in FIG. 3.

Example 4

Construction of Serine Protease Containing Plasmid pMAX-4

To construct plasmid pUCN710 (FIG. 4A) pUB110 was digested with TaqI and PvuII. The fragment containing the gene conferring neomycin resistance was purified on low melting agarose and made blunt with Klenow polymerase and NTP's (Maniatis, *Molecular Cloning: A Laboratory Manual*, Cold Spring Harbor 1982). Plasmid pUC7 (Vieira et al., *Gene* (1982) 19:259–268) was linearized with SalI and made blunt as described above. Both fragments were ligated with T4 ligase (Maniatis) and transformed to *E. coli* JM103. Selection took place on 2xTY plate (1.6% w/v Bactotrypton, 1% w/v yeast extract, 0.5% NaCl) containing 50 µg/ml ampicillin and 10 µg/ml neomycin. The resulting plasmid, named pUCN710, was digested with BamHI. The plasmid pE194 (Jordanescu, *Plasmid* (1978) 1:468–479), which contains a temperature-sensitive origin of replication, was digested with BclI. The fragments from both digestions were ligated with T4 ligase and transformed to *B. subtilis* 1A40. Selection took place on minimal plates containing 20 µg/ml neomycin (see Example 1). The plasmid obtained, pE194-neo (FIG. 4A), contains the neomycin gene.

Subcloning of the protease gene in integration vector pE194-neo was performed as follows: pM58 (see Example 1) was digested with HpaI, BalI and BglII. Plasmid pE194-neo was digested with HpaI. These fragments were ligated with T4 ligase and transformed to *B. subtilis* 1A40. Transformants were selected based upon neomycin resistance and an increase in protease production, as judged by casein cleavage products precipitation (halo formation, see Example 1). Plasmid pMAX-4 was obtained, the structure of which was confirmed by restriction enzyme analysis (see FIG. 4B).

Example 5

Protoplast Transformation of Bacillus Strain PB92 by pMAX-4

Bacillus strain PB92 was grown overnight in 100 ml NBSG-X medium (Thorne et al., *J. Bacteriol.* (1966) 91:1012–1020). The culture was centrifuged for 10 minutes at 4,500 rpm in a Sorvall model GSA rotor. Protoplasts were prepared by incubating the bacilli for one hour at 37° C. in 10 ml Alkaline Holding Medium (AHM) containing 0.5M sucrose, 0.02M $MgCl_2$ and 0.02M Tris/maleate, pH 8.0, in sterile water to which 0.4 mg/ml lysozyme was added. The protoplasts were pelleted (10 minutes at 4,500 rpm), resuspended in 5 ml AHM+ pH 8.0 buffer (AHM buffer to which 3.5% w/v Bacto Penassay Broth and 0.04% w/v Albumine Merieux had been added) mixed, then pelleted as above. After being resuspended in 5.0 ml of alkaline holding medium, 0.5 ml of this suspension of protoplasts were mixed with 5 µl of demineralized water containing 1 µg of plasmid DNA and incubated for 2 minutes in the presence of 30% w/v polyethylene glycol 8,000, pH 8.0. After 1:3 dilution with AHM+ pH 8.0 medium and centrifugation, the pellet was ded in a small volume (1 ml) of AHM+ and incubated for 2-3 hours. One hundred microliter aliquots were plated on freshly prepared regeneration plates containing 0.5M Na succinate/HCl pH 8.0, 1.5% w/v agar, 0.5% w/v casamino acids, 0.5% w/v yeast extract, 0.031M phosphate buffer pH 8.0, 0.5% w/v glucose, 0.02M $MgCl_2$ and 0.02% w/v Albumine Merieux. These plates also contained 1 mg/ml neomycin for selection. After incubation at 37° C. for at least 72 hrs, the colonies were replica-plated onto heart infusion agar plates containing 20 µg/ml neomycin.

Example 6

Integration of pMAX-4 in the Bacillus Strain PB92 Chromosome

A colony of Bacillus strain PB92 containing pMAX-4, grown on a Heart Infusion plate containing 20 µg/ml neomycin, was inoculated in 100 ml Tryptone Soya Broth (TSB) containing 1 µg/ml neomycin and incubated for 24 hours at 37° C. Two ml of the culture (approximately $10^9$ cells/ml) was diluted in 100 ml of the same medium, containing 1 µg/ml neomycin, and incubated for 24 hours at 50° C. After 24 hours, 5 ml of the culture (approximately $10^9$ cells/ml) was diluted again, as described above, and incubated for 24 hours at 50° C. in the presence of 1 µg/ml neomycin. The last procedure was repeated once more. The cell suspension was then diluted a hundred-fold and plated on Heart Infusion (HI) agar (Difco) plates containing 1 µg/ml neomycin. The plates were incubated for 16 hours at 50° C. Neomycin resistant colonies were isolated and cultured in 10 ml TSB medium containing 1 µg/ml neomycin for 16 hours at 37° C. From these cultures, total DNA was isolated (Holmes et al., *Anal. Biochem.* (1981) 114:193–197) and checked for plasmid absence by DNA electrophoresis on agarose gel. Samples in which plasmid DNA was not detectable were rechecked by transformation of total DNA to *B. subtilis* 1A40. Samples lacking the ability to transform *B. subtilis* 1A40 were considered plasmid free. A neomycin resistant, plasmid free, Bacillus PB92 derived strain was isolated and named PBT109. This strain contained a copy of plasmid pMAX-4 integrated into its chromosome.

Integration in strain PBT109 took place through a so-called Campbell-type mechanism by homologous recombination resulting in two tandemly located protease genes on the chromosome separated by plasmid sequences. This genetic organization of strain PBT109 was confirmed as shown in copending U.S. application Ser. No. 162,105 filed concurrently herewith, the disclosure of which is hereby incorporated by reference.

Example 7

Protease Production of the Transformed Strains

Protease production of the transformed strains was tested by adding 0.2 ml of a TSB culture containing approximately $10^9$ cells/ml to 500 ml shake flasks containing 100 ml of the production medium described in U.S. Pat. No. Re. 30,602. When B. subtilis strains were tested, however, the pH was adjusted to pH 7.0. Neomycin was added at a concentration of 20 µg/ml for the strains DB104 (pUB110), DB104 (pMAX-4), PB92 (pMAX-4) and at a concentration of 1 µg/ml for PBT109. The relative protease production for these cell lines is shown in Table 1.

TABLE 1

Production of Protease in Transformed Bacilli

| Strain | Relative Protease Production** | Neomycin Addition |
|---|---|---|
| Bacillus PB92 | 100.0% | — |
| Bacillus PB92 (pMAX-4) | 120.0% | + |
| Bacillus PBT109 | 120.0% | + |
| B. subtilis DB104 (pUB110)* | 1.5% | + |
| B. subtilis DB104 (pMAX-4) | 10.0% | + |

*To measure protease production from the protease gene of pMAX-4 only, this plasmid was also transformed (Spizizen et al., (1961) supra.) to the exoprotease negative B. subtilis strain DB104 (Doi, J. Bacteriol. (1984) 160:442-444) as described in Example 2.
**Protease activity was assayed using dimethyl casein as substrate as described by Lin et al., J. Biol. Chem. (1969) 244:789–793.

In fermentations at a larger scale (10 liters), Bacillus PB92 (pMax-4) showed instability and a decrease in production as compared with PBT109, if no neomycin was added to the fermentation medium.

It is evident from the above results that a simple and efficient procedure is provided for production of serine protease by stably introducing a homologous or heterologous gene encoding serine protease into the chromosome of industrial Bacillus strains. Enhanced production of a serine protease in a Bacillus host which already produces a serine protease is also provided. Integration of plasmid constructs into the host cell chromosomes results in a more stable situation for production fermentations and for a greatly enhanced protease production than when extrachromosomal plasmid constructs are present.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for producing a high alkaline serine protease in an alkalophilic Bacillus host cell, said method comprising:
   introducing into an untransformed parent of said host cell an expression cassette which includes, as operably joined components, (a) a transcriptional and translational initiation regulatory region, (b) a DNA sequence encoding said serine protease, (c) a transcriptional and translational termination regulatory region, wherein said regulatory regions are functional in said host cell, and (d) a selection marker gene for selecting transformed host cells;
   growing said transformed host cells comprising said expression cassette under selective conditions whereby a transformed culture substantially free of untransformed parent cells is obtained; and
   incubating said transformed culture in a nutrient medium, whereby said serine protease is overproduced.

2. A method according to claim 1, wherein an untransformed parent of said host cell is a wild-type Bacillus which produces a serine protease.

3. A method according to claim 1, wherein an untransformed parent of said host cell is a mutant strain of a Bacillus which produces a serine protease.

4. A method according to claim 1, wherein an untransformed parent of said host cell is a mutant strain of a wild-type Bacillus which does not produce a serine protease.

5. A method according to claim 1, wherein an untransformed parent of said host cell is Bacillus novo species PB92.

6. A method for transforming Bacillus cells which comprises:
   pretreating said Bacillus cells with lysozyme in an alkaline medium at about 20° C. to about 37° C. to form protoplasts.

7. A method according to claim 6, wherein said lysozyme concentration is about 0.4 mg/ml alkaline medium.

8. A method according to claim 6, wherein said fusogen is polyethylene glycol at a concentration of about 30% w/v.

9. A method according to claim 6, wherein said DNA construct comprises, in the direction of transcription, a transcriptional and translational initiation regulatory region: a DNA sequence encoding a polypeptide of interest: and a transcriptional and translational termination regulatory region, wherein said regulatory regions are functional in said host cell.

10. A method according to claim 9, wherein said DNA construct further comprises at least one of a selection marker and a temperature-sensitive origin of replication.

11. A method according to claim 6, wherein said Bacillus is an alkalophilic Bacillus.

12. A method for enhancing production of a polypeptide of interest in an alkalophilic Bacillus host cell, said method comprising:
   combining, in the presence of a fusogen at alkaline pH, a protoplast of said host cell and a plasmid construct comprising a DNA sequence encoding an enzyme endogenous to said host cell, a replication system functional in said host cell and a selection marker gene, whereby said DNA is incorporated into said host cell:
   selecting for said host cells containing said DNA: and
   growing said host cells under conditions favoring synthesis of said polypeptide of interest.

13. A method according to claim 12, wherein said host cell is Bacillus novo species PB92.

14. A method according to claim 12, wherein said endogenous enzyme is a serine protease.

15. A method according to claim 14, wherein said serine protease is a high alkaline serine protease.

16. A method according to claim 12, wherein at least one copy of said DNA is incorporated into said host cell.

17. A transformed Bacillus novo species PB92 cell obtained by a method comprising:
isolating a DNA fragment comprising a gene capable of expression in Bacillus novo species PB92 encoding a serine protease;
joining said DNA fragment to linear vector DNA to produce a vector comprising said gene;
combining a protoplast prepared from an untransformed Bacillus novo species PB92 cell with said vector in the presence of a fusogen at alkaline pH, whereby said gene is introduced into said untransformed cell and integrated into the chromosome of said cell to produce a transformed cell; and
selecting a transformed cell stably containing said gene by means of a marker associated with said vector.

18. A method for transforming alkalophilic Bacillus cells, said method comprising:
combining protoplasts formed at high pH from said alkalophilic Bacillus cells with a plasmid construct in the presence of a fusogen.

* * * * *

UNITED STATES PATENT AND TRADEMARK OFFICE
CERTIFICATE OF CORRECTION

PATENT NO. : 5,217,878

DATED : June 8, 1993

INVENTOR(S) : Christiaan A. G. van Eekelen et al.

It is certified that error appears in the above-identified patent and that said Letters Patent are hereby corrected as shown below:

On the title page:
[56] line 8, delete "9/1988" and insert --2/1988--.

Col. 1, line 49, delete "11:7.911" and insert --11:7911--.

Col. 2, lines 30-31, before "DESCRIPTION OF THE DRAWINGS" insert --BRIEF--.

Col. 2, line 46, delete "The lower part of the".

Col. 2, line 31, delete "BRIEF".

Col. 5, line 31, delete "constructor" and insert --construct--.

Col. 7, line 37, before "may" insert --cells--.

Col. 8, line 8, delete "pg/ml" and insert --$\mu$g/ml--.

UNITED STATES PATENT AND TRADEMARK OFFICE
CERTIFICATE OF CORRECTION

PATENT NO. : 5,217,878

DATED : June 8, 1993

INVENTOR(S) : Charistiaan A. G. van Eekelen et al

It is certified that error appears in the above-indentified patent and that said Letters Patent is hereby corrected as shown below:

Col. 10, line 17, delete "ded" and insert --resuspended--.

Signed and Sealed this

Fifth Day of April, 1994

BRUCE LEHMAN

Attest:

Attesting Officer

Commissioner of Patents and Trademarks